United States Patent [19]
Walworth

[11] 3,966,954
[45] June 29, 1976

[54] 3,5-CYCLOALKYL PYRAZOLIUM SALTS AS FUNGICIDES
[75] Inventor: Bryant Leonidas Walworth, Pennington, N.J.
[73] Assignee: American Cyanamid Company, Stamford, Conn.
[22] Filed: Mar. 17, 1975
[21] Appl. No.: 559,000

Related U.S. Application Data
[63] Continuation-in-part of Ser. No. 399,785, Sept. 21, 1973, Pat. No. 3,907,825.

[52] U.S. Cl. .............................................. 424/273
[51] Int. Cl.$^2$......................................... A01N 9/22
[58] Field of Search ............. 260/310, 311; 424/273

[56] References Cited
UNITED STATES PATENTS
3,882,145  5/1975  Walworth et al. ................. 260/311

FOREIGN PATENTS OR APPLICATIONS
2,260,485  6/1973  Germany

OTHER PUBLICATIONS
El-Sokkary et al., Indian J. Pharm., 1973, 35(2), pp. 69–71.
Chemical Abstracts, vol. 79: 27848a (1973).

Primary Examiner—Donald B. Moyer
Attorney, Agent, or Firm—Harry H. Kline

[57] ABSTRACT

There is provided a method for the control of plant pathogenic fungi with certain 3(5) or 3,5-cycloalkyl pyrazolium salts and to a method of protecting plants from fungal attack by applying to the foliage of said plants said pyrazolium salt in fungicidally effective amounts.

14 Claims, No Drawings

3,5-CYCLOALKYL PYRAZOLIUM SALTS AS FUNGICIDES

This application is a continuation-in-part of a copending application, Ser. No. 399,785, filed on Sept. 21, 1973 now U.S. Pat. No. 3,907,825.

The present invention relates to a method for the control of plant pathogenic fungi with pyrazolium compounds having the structure:

(I) $\left[\begin{array}{c}\text{R}_5 \underset{\underset{\text{N}}{\parallel}}{\overset{\overset{\text{CH}_3}{\underset{\mid}{\text{N}}}}{\bigoplus}} \text{N-CH}_3 \\ \text{R}_3\end{array}\right]_m \cdot X^{-m}$ wherein $R_3$ and $R_5$ are each members selected from the group consisting of alkyl $C_4$–$C_{11}$, cycloalkyl $C_3$–$C_7$, phenyl and halogen provided that:

a. when one of $R_3$ and $R_5$ is alkyl $C_4$–$C_{11}$, the other R group is phenyl; or b. when one of $R_3$ and $R_5$ is cycloalkyl $C_3$–$C_7$, the other R group is cycloalkyl $C_3$–$C_7$ or halogen; or c. when one of $R_3$ and $R_5$ is phenyl, the other R group is alkyl $C_4$–$C_{11}$, cycloalkyl $C_3$–$C_7$ or halogen; or d. when one of $R_3$ and $R_5$ is halogen, the other group is phenyl or cycloalkyl $C_3$–$C_7$; X represents an anion with a charge of from 1 to 3; and m is an integer from 1 to 3. More particularly, the invention relates to a method for protecting plants from fungal attack by applying to the foliage of said plants the hereinabove-named compounds in fungicidally effective amounts.

Advantageously the formula (I) pyrazolium salts of the above structure can be prepared readily by reacting a methyl ketone with a carboxylic acid ester, preferably the methyl or ethyl ester, in the presence of an alkali metal hydride, preferably sodium hydride, and an aprotic solvent, such as dimethylsulfoxide (DMSO), dimethylformamide (DMF), xylene, toluene, benzene, or the like. The reaction is generally carried out at a temperature between 0°C. and 40°C., and preferably between 0°C. and 25°C. The reaction yields the β-diketone corresponding to the reactants employed. It is a good practice to react the methyl ketone and carboxylic acid ester in approximately equimolar amounts. However, it is generally desirable to employ a slight excess, i.e. up to about 10 percent excess, of the carboxylic acid ester.

The overall reaction can be illustrated as follows:

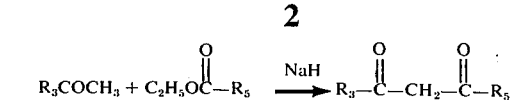

wherein $R_3$ and $R_5$ are as defined above.

Resultant diketone is then condensed with methyl hydrazine to form the corresponding 3,5-disubstituted pyrazole Thereafter, the pyrazole is methylated to form the desired formula (I) pyrazolium salt. These reactions are graphically illustrated below:

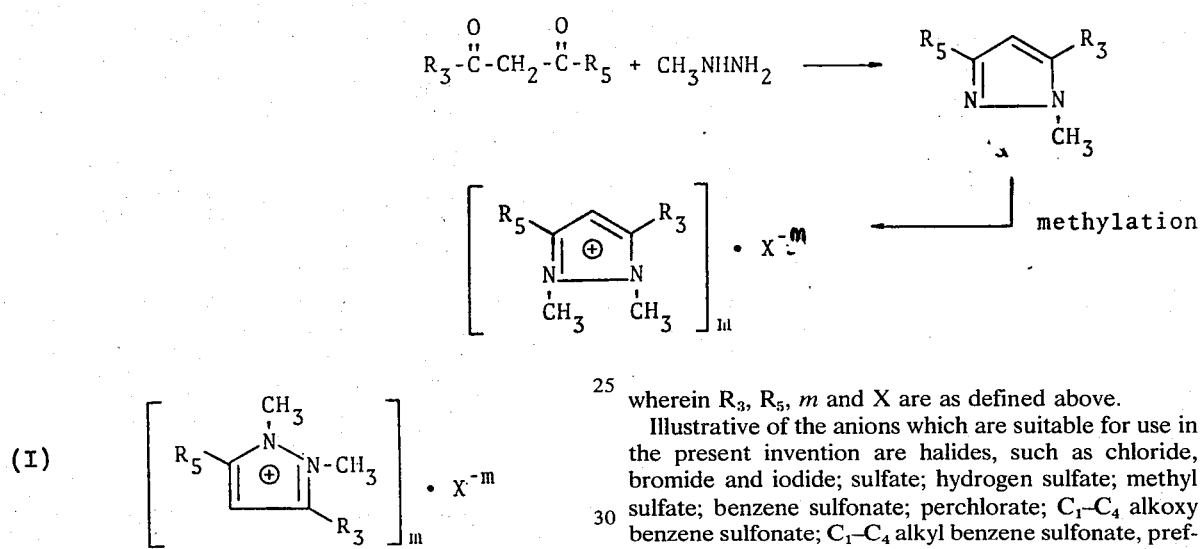

wherein $R_3$, $R_5$, m and X are as defined above.

Illustrative of the anions which are suitable for use in the present invention are halides, such as chloride, bromide and iodide; sulfate; hydrogen sulfate; methyl sulfate; benzene sulfonate; perchlorate; $C_1$–$C_4$ alkoxy benzene sulfonate; $C_1$–$C_4$ alkyl benzene sulfonate, preferably p-toluene sulfonate; phosphate, $C_1$–$C_4$ alkane sulfonate.

In general, equimolar amounts of the diketone with the methyl hydrazine reactant are employed. However, a slight excess (up to about 10 percent) of either reactant may be used. This reaction is usually carried out in the presence of a solvent, either protic or aprotic, at a temperature between about 70°C and 150°C, and preferably between 80°C and 120°C. Preferred solvents for these reactions are protic solvents, such as the lower alcohols including methanol, ethanol, n-propanol, isopropanol, n-butanol and isobutanol. Aprotic solvents which are suitable for use in these reactions include xylene, toluene, benzene, dimethylsulfoxide, dimethylformamide, and pyridine. The introduction of an acid catalyst, such as p-toluene sulfonic acid, increases the rate of the condensation-cyclization reaction.

Advantageously, when hydrazine is used in the initial condensation of the diketone, methylation of the resulting pyrazole is accomplished by means of a known methylating agent, preferably in the presence of an acid acceptor, such as an alkali metal hydroxide, an alkali metal alkoxide, or a tertiary organic amine. Preferred acid acceptors encompass sodium or potassium hydroxide, sodium or potassium methoxide, ethoxide, propoxide or t-butoxide, trimethylamine, triethylamine and pyridine.

Methylation of the pyrazole is usually carried out in the presence of a solvent at a temperature between 50°C and 200°C, and preferably between 90°C and 120°C. Preferred solvents include aromatic hydrocarbons such as toluene, xylene and chlorobenzene; ketones having 4 to 7 carbon atoms such as the methylisobutylketone (MIBK) and methylbutylketone (MBK); $C_2$–$C_5$ alcohols; dipolar aprotic solvents such as dimethylsulfoxide (DMSO), dimethylformamide (DMF), acetonitrile, nitrobenzene and N,N-dimethylacetamide; and cyclic ethers such as dioxane and tetrahydrofuran.

Exemplary of the methylating agents are: methyl halides, dimethyl sulfate, methyl phosphate, methyl hydrogen sulfate, and methyl toluene sulfonate. Among the preferred methylating reagents are the methyl halides such as methyl chloride and bromide; dimethyl sulfate, methyl hydrogen sulfate, and toluene sulfonate. While the 3,5-disubstituted pyrazoles combine with equimolar amounts of the methylating agent, it is a good practice to employ an excess of methylating reagent. Mole ratios of methylating reagent to pyrazole within the range of from 1:1 to 1.5:1 are preferred.

In reactions involving methylation, it is found that on cooling of the reaction mixture the solid or oily pyrazolium salt separates and is purified by separation from the organic layer. However, in instances, particularly those wherein $R_3$ and $R_5$ are highly lipophilic (e.g. the 3,5-dicyclohexyl and 3-cyclohexyl-5-phenyl), separation of the pyrazolium salt from the organic phase cannot be readily accomplished. However, the product can be obtained by the evaporation of the solvent, and dissolving the residue in chloroform, water washing of the chloroform layer, and evaporation of the chloroform to obtain the pyrazolium salt as the residue.

Utilizing toluene sulfonates or methyl sulfates as alkylating agents, impure or hygroscopic materials are frequently obtained due to anion contaminations (such as $HSO_4^-$ or $SO_4^{--}$). In such instances, the mixed anion is purified by passing an aqueous solution of this mixture through an anion exchange column. Alternatively, the aqueous solution of mixed anions can be converted to an iodide using aqueous saturated potassium iodide or sodium iodide solution. The latter treatment yields the relatively water-insoluble iodide. Perchlorates are prepared by the addition of dilute aqueous perchloric acid to an aqueous pyrazolium salt solution to give the waterinsoluble perchlorate. Additionally pure pyrazolium salts, e.g. $CH_3SO_4^-$, $HSO_4^-$, $SO_4^{--}$ or $Cl^-$ may be converted by the abovementioned procedures of anion exchange chromatography to a new pyrazolium salt, and to iodides and perchlorates as defined above. The pyrazolium halides are prepared as hereinabove described, except that the reaction is conducted in a sealed vessel or glass-lined bomb maintained at a temperature of about 100°C.

The pyrazolium compounds of this invention are useful as fungicidal agents and are particularly effective when applied to the foliage of plants. They are employed at rates between about 0.28 kg per hectare and 11.2 kg per hectare, and preferably used at rates between 0.56 kg and 5.6 kg per hectare.

Formula (I) pyrazolium salts where $R_3$, $R_5$, $m$ and X are as defined above, exhibit excellent foliar fungicidal activity.

Advantageously, many of the formula I pyrazolium salts demonstrate a high degree of water solubility and lend themselves to the preparation of aqueous concentrates. Among the preferred salts are the methyl sulfates, hydrogen sulfates, sulfates, chlorides and bromides. In practice, the aqueous concentrates may be applied directly as a liquid spray to the foliage of plants. Alternatively, they may be further diluted with water and applied as dilute aqueous sprays to these plants.

Emulsifiable concentrates are prepared by dissolving from 15 to 95 percent of the compound in 85 to 5 percent of a watermiscible solvent, such as water itself or another polar watermiscible solvent, such as 2-methoxy ethanol, methanol, propylene glycol, diethylene glycol, diethylene glycol monoethyl ether, formamide and dimethylformamide. Application of the material is made by adding a predetermined quantity of the emulsifiable concentrate to a spray tank and applying the mixture as such or in combination with a suitable diluent, such as a further quantity of water or one of the above polar solvents.

The performance of the product in all of the above formulations, which are applied as liquid sprays, is unexpectedly improved by adding a surfactant or blend of surfactants. Conventional anionic, cationic and anionic-nonionic surfactants may be employed.

Illustrative nonionic surfactants are: alkyl polyoxyethylene ethers, polyoxyethylene (20) sorbitan monolaurate, polyoxyethylene (20) sorbitan monooleate, alkylarylpolyglycol ethers, alkyl phenol ethoxylates, trimethyl nonyl polyethylene glycol ethers, alkyl phenol ethylene oxide condensates, octyl phenoxy polyethoxy ethanols, nonylphenyl polyethylene glycol ethers, condensates of polyoxyethylenes, polyoxypropylenes, aliphatic polyethers, aliphatic polyesters, alkylaryl polyoxyethylene glycols, and the like.

Exemplary anionic surfactants include sodium dodecylbenzene sulfonate and the dioctyl ester of sodium sulfosuccinic acid.

Suitable cationic surfactants include: dicoco dimethylammonium chloride, stearamidopropyl dimethyl betahydroxy-ethylammonium nitrate, and the like.

These surfactants are preferably added to the spray tank at the rate of 0.1% to 5% by volume to provide good wetting of the spray solution on plant foliage.

Fungicidal concentrates containing surfactants are preferably formulated as aqueous sprays containing approximately 30% by weight of the appropriate salt, from about 25 to 50% by weight of water and the remainder of said formulation (25 to 45% by weight) of a selected surfactant. Surfactants which are especially useful in preparating suitable surfactant-containing concentrates include an octylphenol ethylene oxide condensate, an ethanolic solution of an alkyl phenol ethoxylate, a polyglycolic ether condensate produced from ethylene oxide, and an alkyl phenol, and an alkylaryl polyglycolic ether.

Other formulations which may be used to advantage with the compounds of this invention include dusts, dust concentrates and wettable powders.

Dusts are generally prepared by grinding together about 1% to 25% by weight of the active agent with from about 99% to 75% by weight of a solid diluent such as kaolin, attapulgite, talc, pumice, diatomaceous earth, fullers earth, wood flour, or the like.

Dust concentrates are prepared in similar fashion excepting that about 25 to 95% by weight of the active agent is ground with about 75 to 5% by weight of the diluent.

Wettable powders are prepared in the same manner as the dust concentrates excepting that about 1 to 5% by weight of a dispersing agent such as the calcium salt of a polymerized alkylaryl sulfonic acid, sodium lignosulfonate, or sodium salt of condensed naphthalene sulfonic acid is blended with the mixture and about 1 to 5% of a surfactant, such as polyoxyethylated vegetable oil, alkyl phenoxy polyoxyethylene ethanol, sodium alkyl naphthalene sulfonate is also blended with the formulations.

In practice, the wettable powder is dispersed in water and applied as a liquid spray to the foliage of plants.

Application rates should be sufficient to provide about 0.28 kg to 11.2 kg per hectare of the pyrazolium salt, and preferably 0.56 kg to 5.6 kg per hectare of said salt.

In order to facilitate a further understanding of the invention, the following examples are presented primarily for the purpose of illustrating certain more specific details thereof. The invention is not to be deemed limited thereby, except as defined in the claims. Unless otherwise noted, all parts are by weight.

EXAMPLE 1

Preparation of 1,3-Dicyclohexyl-1,3-propanedione

Sodium hydride (39.5 g of 54%, 0.889 mol) is cooled with an ice bath to 18°C in a suitable flask fitted with stirrer, condenser, drying tube, dropping funnel and thermometer. Dimethyl sulfoxide (700 ml), dried over 4A molecular sieves, is slowly added. After addition is complete, the reaction mixture is stirred for 0.5 hour at room temperature. The ice bath is replaced and a mixture of cyclohexanecarboxylic acid, ethyl ester (138.8 g, 0.889 mol) and cyclohexyl methyl ketone (101.9 g, 0.80 mol) are added dropwise. No exotherm is observed. The reaction mixture becomes lighter in color and some bubbles are observed. After the addition has been completed, the ice bath is removed and the reaction mixture is stirred overnight at room temperature. The thick, deep buff-colored reaction mixture is poured over ice (8 liters) containing phosphoric acid (50 ml) and extracted with ether. The ether is washed with water, dried and vacuum stripped to yield a golden yellow oil (204 g) which smells strongly of the ester. The product is purified via the copper complex as set forth in the *Journal of Organic Chemistry* 13, 160 (1948) to yield white crystals having a melting point of 50°C to 52°C.

Analysis Calculated for $C_{15}H_{24}O_2$: C, 76.22; H, 10.24. Found: C, 76.20; H, 10.03.

Other β-diketones can be prepared from esters and ketones containing $R_3$ and $R_5$ as previously defined. Thus, 1-cyclopropyl-3-phenyl-1,3-propanedione has been reported by G. W. Cannon et al., *Journal of Organic Chemistry* 17, 685 (1952) to be prepared as a solid, melting point 36°C to 37°C, from ethyl benzoate and cyclopropyl methylketone in the presence of sodium amide. Alternatively, it has been found that the same compound, melting point 38°C to 40°C, could be prepared from ethyl cyclopropanecarboxylate, acetophenone and sodium hydride. J. T. Adams and C. R. Hauser in *Journal of the American Chemical Society* 66, 1220 (1944) have prepared a series of 1-alkyl-3-phenyl-1,3-propanediones from carboxylic acid ethyl esters and acetophenone in the presence of sodium amide. Illustrative examples are tabulated employing the following equation:

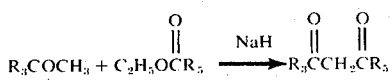

$$R_3COCH_3 + C_2H_5OCR_5 \xrightarrow{NaH} R_3CCH_2CR_5$$

where $R_3$ and $R_5$ are set forth in the Table I below.

TABLE 1

| $R_3$ | $R_5$ | Melting Point °C | Appearance |
|---|---|---|---|
|  |  | 38–40 | Cream crystals |
|  |  | 48.5–50 | White solid |
|  |  | (boiling point 155–160°/0.5 mm) | Colorless oil |
|  |  | oil | Orange oil |

Other propanediones which can be prepared by the above procedure using the appropriate carboxylic acid esters and substituted methyl ketones are:

1,3-Dicyclohexyl-1,3-propanedione;
1-Phenyl-3-cycloheptyl-1,3-propanedione;
1,3-Dicyclopropyl-1,3-propanedione; and
1-cyclopentyl3-phenyl-1,3-propanedione.

EXAMPLE 2

Preparation of 3-Cyclopropyl-1-methyl-5-phenylpyrazole and 5-Cyclopropyl-1-methyl-3-phenylpyrazole 1-Cyclopropyl-3-phenyl-1,3-propanedione (37.6 g, 0.2 mol) and 2-propanol (250 ml) are heated to reflux. Methyl hydrazine (10.2 g, 0.22 mol) is then added dropwise, and the solution refluxed until the reaction is complete (2.5 hours). The solution is then filtered and vacuum stripped to give a yellow oil (39.2 g, 99%). Examination of the product on a silica gel tlc plate developing with chloroform and iodine shows the presence of an impurity. The product is chromatographed on silica gel with chloroform to give a white, cloudy oil.

Analysis Calculated for $C_{13}H_{14}N_2$: C, 77.68; H, 7.26; N, 13.52. Found: C, 77.92; H, 7.33; N, 13.56.

EXAMPLE 3

The following pyrazoles of the structure:

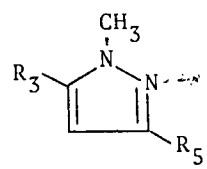

are prepared by the method of Example 2 above, employing the appropriate 1,3-propanedione as a substitute for 1-cyclopropyl-3-phenyl-1,3-propanedione. The results of the process are set forth in Table II (Ex A-F) below.

TABLE II

| Ex | R₅ | R₃ | Melting Point °C | Appearance | Method of Purification |
|----|----|----|------------------|------------|------------------------|
| A | cyclopentyl | phenyl | Oil | Yellow Oil | Chromatographed on silica gel with CHCl₃ |
| B | cycloheptyl | phenyl | Oil | Yellow Oil | via The hydrochloride salt |
| C | cyclohexyl | cyclohexyl | 47 | White Solid | Recrystallization from n-pentane |
| D | cyclohexyl | phenyl | Oil | Yellow Oil | Low temperature recrystallization from hexane |
| E | cyclohexyl | cyclohexyl | 47 | white solid | Low temperature recrystallization from hexane |
| F | cyclopropyl | phenyl | Oil | Yellow Oil | Low temperature recrystallization from hexane |

Another pyrazole that can be prepared by the above procedure employing the appropriate 1,3-propanedione is 3,5-dicyclopropyl-1-methylpyrazole.

EXAMPLE 4

Preparation of 3-Cyclohexyl-1,2-dimethyl-5-phenylpyrazolium methyl sulfate

1-Methyl-3(5)-cyclohexyl-5(3)-phenyl pyrazole (8.0 g, 0.033 mol) is dissolved in dry toluene and warmed to ~65°C. Dimethyl sulfate (4.5 g, 0.035 mol) is then added and the mixture is brought to reflux. Tlc (benzene) after 1 ½ hours shows a small amount of pyrazole remaining. After 2 hours the reaction mixture begins darkening and heating is discontinued. On cooling a white solid forms which is filtered and washed with dry toluene. This tacky white solid is vacuum dried at room temperature to give a brittle solid. Hexane is then added and the solid broken up and collected by filtration. The solid (6.3 g, 50% yield) has melting point 48°C to 51°C. On exposure to air it becomes tacky (hygroscopic). On analysis the following is noted.

Analysis Calculated for $C_{18}H_{26}N_2SO_4 \cdot H_2O$: C, 56.24; H, 7.34; N, 7.29. Found: C, 56.91; H, 7.33; N, 7.12.

EXAMPLE 5

Preparation of 5-Cyclopropyl-1,2-dimethyl-3-phenylpyrazolium methyl sulfate

A mixture of 3-cyclopropyl-1-methyl-5-phenyl pyrazole and 5-cyclopropyl-1-methyl-3-phenylpyrazole (33.1 g, 0.167 mol) and dry toluene (250 ml) are heated to reflux and approximately 25 ml of solvent removed with a Dean Stark trap. The solution is next cooled and dimethyl sulfate (18 ml, 0.193 mol) added. The reaction mixture is held at 100°C for 2.5 hours. A yellow brown oil is formed which solidifies upon cooling. The solid is removed by filtration and dried under vacuum giving a cream-colored solid (49.5 g, 91.5%) having a melting point equal to 163°C to 170°C whose analysis is as follows:

Analysis Calculated for $C_{15}H_{20}N_2SO_4$: C, 55.54; H, 6.22; N, 8.64; S, 9.89. Found: C, 55.27; H, 6.23; N, 9.48; S, 9.99.

The following pyrazoles when reacted with dimethyl sulfate, using the above method, yield products which are a mixture of methyl sulfate and hydrogen sulfate salts. In such instances, the products are converted completely to the iodides and/or perchlorate salts by dissolving in water and treating the same with saturated potassium (or sodium) iodide or dilute perchloric acid, respectively. For instance, utilizing either (1) 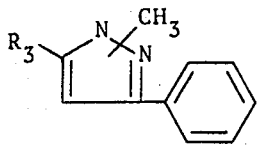

where R₃ is cycloheptyl-, or (2) 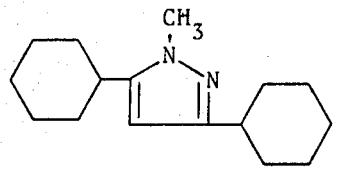

the methyl sulfate/hydrogen sulfate salts, when employing the cycloheptyl group, do not separate upon cooling the reaction mixture. In these cases, the reaction mixture is vacuum stripped, the residue dissolved in water and used for making the iodide and/or perchlorate without any solvent extraction.

EXAMPLE 6

Preparation of 5-Cyclopropyl-1,2-dimethyl-3-phenylpyrazolium perchlorate.

An aqueous solution (500 ml) containing 10 g of 5-cyclopropyl-1,2-dimethyl-3-phenylpyrazolium methyl sulfate is extracted with ether. The aqueous layer is separated and treated with dilute perchloric acid (10 ml) to give a solid. After stirring for one hour, the solid is removed by filtration and dried to give a cream-colored solid (6.1 g, 60%) with melting point 160°C to 161°C. On analysis, the following is obtained:

Analysis Calculated for $C_{14}H_{17}ClN_2O_4$: C, 53.75; H, 5.48; N, 8.96; Cl, 11.34. Found: C, 54.0; H, 5.40; N, 8.90; Cl, 11.48.

As noted in Table III (G, $G_1$, $G_2$, H, I) below, several exemplary perchlorates are prepared by the method as described in Example 6 above, using the appropriate pure, technical or crude 1,2-dimethyl-3,5-substituted pyrazolium methyl sulfate salt as starting material of the structure:

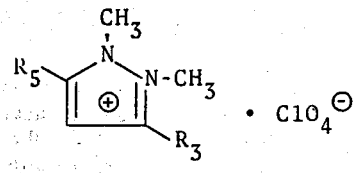

EXAMPLE 7

Preparation of 5-Cyclopropyl-1,2-dimethyl-3-phenylpyrazolium iodide

A solution of 5-cyclopropyl-1,2-dimethyl-3-phenylpyrazolium methyl sulfate (12.3 g) dissolved in water (100 ml) is extracted with ether. The aqueous layer is separated and treated with a saturated aqueous solution of potassium iodide. After stirring for 0.5 hour, the solid is separated by filtration and dried to give a straw-colored solid (4.7 g, 36%) with melting point 150°C to 152°C. On analysis, the following is noted.

Analysis Calculated for $C_{14}H_{17}N_2I$: C, 49.42; H, 5.04; N, 8.24. Found: C, 49.07; H, 5.06; N, 8.16.

Illustrative iodides in Table IV (j, K, $K_1$, L) below are prepared by the method as described above in Example 7, substituting the appropriate pyrazolium methyl sulfate salt for 5-cyclopropyl-1,2-dimethyl-3-phenylpyrazolium methyl sulfate of the structure:

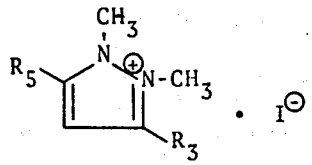

TABLE IV

| Ex | $R_5$ | $R_3$ | Melting Point °C | Appearance |
|---|---|---|---|---|
| J | cyclopropyl | phenyl | 150–152 | Straw-colored solid |
| K | cyclohexyl | phenyl | 129–131 | Faint yellow solid |
| $K_1$ | n-$C_{11}H_{23}$ | phenyl | 74–76 | Buff-colored solid |

TABLE III

| Ex | $R_5$ | $R_3$ | Melting Point °C | Appearance |
|---|---|---|---|---|
| G | n-pentyl | phenyl | 104–105 | Off-white solid |
| $G_1$ | t-butyl | phenyl | 142–146 | Cream-colored solid |
| $G_2$ | cyclopropyl | phenyl | 75–76 | Off-white solid |
| H | cyclohexyl | phenyl | 115–116 | Off-white solid |
| I | phenyl | phenyl | 73–80 | Beige solid |

TABLE IV-continued

| Ex | R₅ | R₃ | Melting Point °C | Appearance |
|---|---|---|---|---|
| L | (phenyl) | (phenyl) | 226–227 | Cream-colored solid |

EXAMPLE 8

Preparation of 3-Chloro-1,2-dimethyl-5-phenylpyrazolium methyl sulfate/sulfate and perchlorate salts 3-Chloro-2-methyl-5-phenylpyrazole (7.0 g, 0.0352 mol) and dimethyl sulfate (8.82 g, 0.07 mol) are mixed and heated to a bath temperature of 80°C. The internal reaction temperature rises to 88°C, thereafter the reaction is maintained at a bath temperature of 88°C (internal temperature: 80°C) for 6 hours. The reaction mixture is then cooled to room temperature and toluene (10 ml) added. After standing overnight at room temperature, a waxy solid separates out and is filtered off. The waxy solid is recrystallized from methylene chloride/ether to afford 11.2 g of a granular material, melting point 70°C to 73.5°C.

Nmr indicates that the salt obtained is a 1:1 mixture of the pyrazolium methyl sulfate and hydrogen sulfate. The sample is dried in vacuo at 30°C.

A small sample of the above-mixed salt is recovered from the mother liquor by evaporating it to dryness. The sample is dissolved in water and ice cold 10% perchloric acid is added to the solutions. A white solid precipitates which is filtered and washed with water to give 120 mg of the perchlorate, melting point 216°C to 218°C.

EXAMPLE 9

Preparation of 3-Chloro-2-methyl-5-phenylpyrazole

2-Methyl-5-phenylpyrazol-3-one (7.9 g, 0.0429 mol) is added to phosphorus oxychloride (15.3 g). The mixture is stirred at 120°C to 135°C for 8 hours, then poured into ice water, made alkaline and extracted with methylene chloride. The solution is evaporated in vacuo at 90°C to yield 8.0 g (93.8%) of an oil.

Analysis Calculated for $N_2ClC_{10}H_{15}$: C, 60.45; H, 7.61; N, 14.10; Cl, 17.85. Found: C, 60.28; H, 7.55; N, 14.20; Cl, 17.79.

EXAMPLE 10

To determine the effectiveness of pyrazolium salts as foliar fungicidal agents, a variety of pathogenic fungi, host plants and pyrazolium salts are used in the following tests. Pathogens, host plants, the method of testing and the rating system used are reported below along with the data obtained.

Pathogens:

*Piricularia oryzae* Carvara, the rice blast pathogen.
*Venturia inacqualis* (Cke.) Wint., which causes apple scab.
*Erysiphe cichoracearum* DC, the cause of powdery mildew on cucumbers.
*Podosphaera leucotricha* (E.&E.) Salm., the cause of powdery mildew on apples and pears.
*Erysiphe graminis* f. sp. tritci, the cause of powdery mildew on wheat.
*Erysiphe graminis* f. sp. hordei, the cause of powdery mildew on barley.
*Phytophthora infestans* (Mont.) Dby., the late blight fungus of tomato and potato.

Host Plants:

Rice (*Oryza sativa*, Cv. Nato)
Cucumber (*Cucumis sativus*, Cv. Marketer)
Apple (*Malus sylvestris*, Seedling)
Wheat (*Triticum aestivum*, Cv. Bonanza)
Tomato (*Lycopersicon esculentum*, Cv. Bonny Best)
Barley (*Hordeum vulgare*, Cv. Larker)

Plants are individually grown in 5.08 cm peat squares and assembled in 7.62 cm × 25.4 cm pressed fibre flats the week prior to spraying. With the exception of rice, barley and wheat, a single specimen of each species is used. A separate container is used for those plants in the mildew evaluation. The complete test system is shown below.

| Series 1 | Series 2 |
|---|---|
| Rice: Rice Blast | Apple: Powdery Mildew |
| Apple: Apple Scab | Wheat: Powdery Mildew |
| Tomato: Late Blight | Barley: Powdery Mildew |
| | Cucumber: Powdery Mildew |

Spray solutions are prepared at a final concentration of 500 ppm in 50 ml of 50% aqueous acetone. In all cases, acetone is added first to solubilize the compound and solutions made to final volume with deionized water.

Two flats, one containing the host plants for Series 1 and one containing the host plants for Series 2, are sprayed simultaneously on a turntable with 50 ml of the test solution. Spray is provided by two fixed Spray System Company nozzles mounted to deliver vertical and horizontal solid cone patterns. Immediately thereafter, all plants are returned to the greenhouse to permit deposit to dry.

After the plants have dried, Series 1 and 2 are separately inoculated. Plants in Series 1 are inoculated with conidial suspensions of the respective pathogens using a Devilbiss paint sprayer operated at 0.28 kg to 0.42 kg/cm² and immediately transferred to a controlled temperature/humidity cabinet (ambient temperature, rh~95 percent). Plants in Series 2 are dusted with respective powdery mildew conidia and then removed to a plant culture room (10 hours light, 70° to 74°F, 45% rh) to await disease development. All plants are rated for disease severity on a scale of 1 to 7 (clean to kill), as described below:

| Rating | Description |
|---|---|
| 1 | Nil |
| 2 | Trace disease |
| 3 | Slight disease |
| 4 | Moderate disease |
| 5 | Heavy disease |
| 6 | Severe disease |

| Rating | -continued Description |
|---|---|
| 7 | Kill |

Data obtained are reported in Tables V and VI below. Ratings reflect only levels where effective control was observed and are mean ratings for all tests carried out with any given compound.

TABLE V

Disease Severity of Plants Sprayed to Run-off with Indicated Minimum Effective Rates (ppm)
(Series 1)

| Compound | Rice Blast 500 | Rice Blast 100 | Tomato Late Blight 500 | Tomato Late Blight 100 | Apple Scab 500 | Apple Scab 100 |
|---|---|---|---|---|---|---|
| Untreated Controls; Average Rating | 5.3 | | 6.3 | | 5.5 | |
| Pyrazolium methyl sulfate, 5-cyclohexyl-1,2-dimethyl-3-phenyl | | | | | 3.0 | |
| Pyrazolium iodide, 3,5-dicyclohexyl-1,2-dimethyl | | 4.0 | 1.0 | | 5.0 | |
| Pyrazolium perchlorate, 3,5-dicyclohexyl-1,2-dimethyl | 5.0 | | | | 5.0 | |
| Pyrazolium methyl sulfate, 5-cyclopropyl-1,2-dimethyl-3-phenyl | | | 5.5 | | 5.0 | |
| Pyrazolium iodide, 5-cyclopropyl-1,2-dimethyl-3-phenyl | | | | | 4.2 | |
| Pyrazolium methyl sulfate, 5-cyclopropyl-1,2-dimethyl-3-phenyl | 5.0 | | | | 5.0 | |
| Pyrazolium perchlorate, 5-cyclopropyl-1,2-dimethyl-3-phenyl | 5.0 | | 5.7 | | | |
| Pyrazolium iodide, 5-cycloheptyl-1,2-dimethyl-3-phenyl | | | | | 4.0 | |
| Pyrazolium perchlorate, 3-cyclohexyl-1,2-dimethyl-5-phenyl | | | | | 5.0 | |
| Pyrazolium perchlorate, 3-chloro-5-cyclohexyl-1,2-dimethyl | | 5.0 | 5.0 | | | 4.0 |

TABLE VI

Disease Severity of Plants Sprayed to Run-off with Indicated Minimum Effective Rates (ppm)
(Series 2)

| Compound | Cucumber Powdery 500 | Wheat Powdery 500 | Apple Powdery 500 | Barley Powdery 500 |
|---|---|---|---|---|
| Untreated Controls; Average Rating | 5.8 | 5.7 | 5.4 | 6.0 |
| Pyrazolium methyl sulfate, 5-cyclohexyl-1,2-dimethyl-3-phenyl | 4.0 | 2.5 | 2.5 | |
| Pyrazolium iodide, 3,5-dicyclohexyl-1,2-dimethyl | 5.0 | 1.0 | 5.0 | |
| Pyrazolium perchlorate, 3,5-dicyclohexyl-1,2-dimethyl | | 3.0 | | |
| Pyrazolium methyl sulfate, 5-cyclopropyl-1,2-dimethyl-3-phenyl | | 2.8 | 3.8 | 4.5 |
| Pyrazolium iodide, 5-cyclopropyl-1,2-dimethyl-3-phenyl | 5.0 | 3.4 | | 5.0 |
| Pyrazolium methyl sulfate, 3-cyclopentyl-1,2-dimethyl-5-phenyl | | 2.5 | 5.0 | |
| Pyrazolium perchlorate, 5-cyclopropyl-1,2-dimethyl-3-phenyl | | | 3.3 | |
| Pyrazolium iodide, 5-cycloheptyl-1,2-dimethyl-3-phenyl | 5.0 | 5.0 | 5.0 | |
| Pyrazolium iodide, 3-cyclohexyl-1,2-dimethyl-5-phenyl | 3.0 | 1.0 | 3.0 | |
| Pyrazolium perchlorate, 3-cyclohexyl-1,2-dimethyl-5-phenyl | | 3.0 | 4.0 | |
| Pyrazolium methyl sulfate/sulfate (1:1), 3-chloro-5-cyclohexyl-1,2-dimethyl | | 4.0 | | |
| Pyrazolium perchlorate, 1,2-dimethyl-5-n-pentyl-3-phenyl- | | 2.0 | 4.0 | |
| Pyrazolium methylsulfate, 1,2-dimethyl-5-n-pentyl-3-phenyl- | | 2.5 | 4.0 | |
| Pyrazolium perchlorate, 1,2-dimethyl-5-t-butyl-3-phenyl- | | 4.0 | 5.0 | |
| Pyrazolium methyl sulfate, 1,2-di-3-phenyl-5-n-undecyl- | | 1.5 | 4.0 | |

I claim:

1. A method for controlling disease growth and protecting plants from attack by plant pathogenic fungi comprising, applying to said plants which are to be protected a fungicidally effective amount of a compound having the formula:

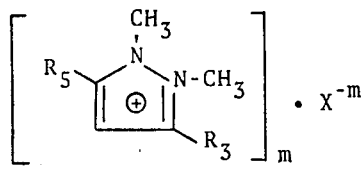

wherein $R_3$ and $R_5$ are members independently selected from the group consisting of alkyl $C_4$–$C_{11}$, phenyl, cycloalkyl $C_3$–$C_7$, and halogen provided that:
 a. when one of $R_3$ and $R_5$ is alkyl $C_4$–$C_{11}$, the other R group is phenyl; or
 b. when one of $R_3$ and $R_5$ is cycloalkyl $C_3$–$C_7$, the other R group is cycloalkyl $C_3$–$C_7$ or halogen; or
 c. when one of $R_3$ and $R_5$ is phenyl, th other R group is alkyl $C_4$–$C_{11}$, cycloalkyl $C_3$–$C_7$ or halogen; or
 d. when one of $R_3$ and $R_5$ is halogen, the other group is phenyl or cycloalkyl $C_3$–$C_7$; X represents an anion having a charge of from 1 to 3 and is selected from the group consisting of bromide, chloride, iodide, acetate, sulfate, hydrogen sulfate, methyl sulfate, benzene sulfonate, p-toluene sulfonate, nitrate, phosphate, carbonate, perchlorate and mixed sulfate/hydrogen sulfate; m is an integer selected from 1, 2 and 3.

2. The method according to claim 1 wherein said compound is 3-chloro-1,2-dimetyl-5-phenylpyrazolium methyl sulfate/hydrogen sulfate mixed salt.

3. The method according to claim 1 wherein said compounds is 3-chloro-1,2-dimethyl-5-phenylpyrazolium perchlorate.

4. The method according to claim 3, wherein said compound is 5-cyclohexyl-1,2-dimethyl-3-phenylpyrazolium methyl sulfate.

5. The method according to claim 1, wherein said compound is 3,5-dicyclohexyl-1,2-dimethylpyrazolium iodide.

6. The method according to claim 1, wherein said compound is 3,5-dicyclohexyl-1,2-dimethylpyrazolium perchlorate.

7. The method according to claim 1, wherein said compound is 5-cyclopropyl-1,2-dimetyl-3-phenylpyrazolium iodide.

8. The method according to claim 1, wherein said compound is 5-cyclopropyl-1,2-dimethyl-3-phenylpyrazolium methyl sulfate.

9. The method according to claim 1, wherein said compound is 5-cyclopropyl-1,2-dimetyl-3-phenylpyrazolium perchlorate.

10. The method according to claim 1, wherein said compound is 5-cycloheptyl-1,2-dimethyl-3-phenylpyrazolium iodide.

11. The method according to claim 1, wherein said compound is 3-cyclohexyl-1,2-dimethyl-5-phenylpyrazolium perchlorate.

12. The method according to claim 1, wherein said compound is 3-chloro-5-cyclohexyl-1,2-dimethylpyrazolium perchlorate.

13. The method according to claim 1, wherein said compound is applied to plant pathogenic fungi in an amount sufficient to provide from 0.56 kg to 11.2 kg per hectare of said active compound.

14. The method according to claim 1, wherein said compound is applied to plant pathogenic fungi in an amount sufficient to provide from 0.56 kg. to 4.48 kg. per hectare of said active compound.

* * * * *